United States Patent [19]

Chang et al.

[11] 4,365,103

[45] Dec. 21, 1982

[54] PROCESS FOR THE PREPARATION OF BIS(1-PHENYLETHENYL) COMPOUNDS

[75] Inventors: Kuo Y. Chang; Sterling C. Gatling, both of Midland, Mich.

[73] Assignee: The Dow Chemical Company, Midland, Mich.

[21] Appl. No.: 327,322

[22] Filed: Dec. 4, 1981

[51] Int. Cl.$^3$ ............................................. C07C 15/12
[52] U.S. Cl. .................................. 585/320; 585/436; 585/471; 585/472
[58] Field of Search ............... 585/320, 436, 471, 472

[56] References Cited

U.S. PATENT DOCUMENTS

| 4,115,464 | 9/1978 | Bartek et al. | 585/436 |
| 4,172,100 | 10/1979 | Tung et al. | 585/320 |
| 4,236,035 | 11/1980 | Sigwelt et al. | 585/436 |

FOREIGN PATENT DOCUMENTS 1180459  2/1970  United Kingdom ............... 585/472

*Primary Examiner*—Curtis R. Davis
*Attorney, Agent, or Firm*—R. B. Ingraham

[57] ABSTRACT

A 1,1-diphenylethane and an aromatic compound such as benzene are reacted in the presence of a Friedel-Craft's catalyst to provide a compound having two 1,1-diaromatic substituted ethane groups, dehydrogenation provides a bis(1-phenylethenyl)aromatic compound.

9 Claims, No Drawings

PROCESS FOR THE PREPARATION OF BIS(1-PHENYLETHENYL) COMPOUNDS

Bis(1-phenylethenyl)aromatic compounds are highly desirable as chemical intermediates in the preparation of difunctional lithium initiators for anionic polymerization of 1,3-butadiene, vinyl aromatics and the like. Such initiators and their preparation are well known and set forth in such patents as U.S. Pat. Nos. 4,172,100; 4,172,190; 4,182,818; 4,196,153; 4,196,154; 4,200,718; 4,201,729; 4,196,115; 4,205,016, as well as European patent application No. 0025942. Other patent and literature references to this general type of initiator also exist. A particularly desirable initiator is prepared from meta-bis-1-phenylethenyl benzene when reacted with 2 moles of normal or secondary butyllithium. The meta substituted benzene compound is particularly desirable in that the initiators are soluble in hydrocarbon solvents generally employed in the polymerization of butadiene, styrene and the like. Such meta compounds are set forth in U.S. Pat. Nos. 4,172,100; 4,172,190; 4,196,154. The methods of synthesis set forth in the prior art for the bis(1-phenylethenyl)benzene compounds are cumbersome, time consuming, and generally inefficient, although operable.

It would be desirable if there were available an improved method for the preparation of bis(1-phenylethenyl)aromatic compounds.

It would also be desirable if such a method involved a minimum number of steps and provided the desired product at an acceptable yield level.

These benefits and other advantages in accordance with the present invention are achieved in a method for the preparation of bis(1-phenylethenyl)aromatic compounds, the steps of the method comprising providing a 1,1-diphenylethane, disproportionating the 1,1-diphenylethane in the presence of a Friedel-Craft's catalyst to form a bis(1-phenylethyl)aromatic compound and subsequently dehydrogenating the bis(1-phenylethyl)aromatic compound to a bis(1-phenylethenyl)aromatic compound.

The invention is further illustrated but not limited by the reaction scheme.

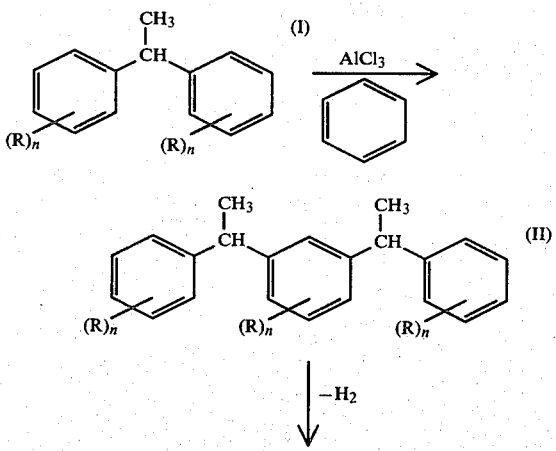

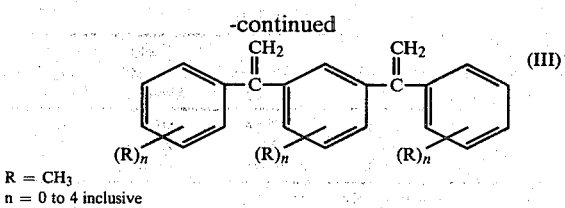

R = CH$_3$
n = 0 to 4 inclusive wherein R is a methyl group and n is individually from 0 to 4 inclusive. In the absence of a methyl group attached to an aromatic ring, a hydrogen is attached to the ring.

This disproportionation of compound 1 to compound 2 is readily accomplished by treating compound 1 with a Friedel-Craft's catalyst such as aluminum chloride, borontrifluoride, tintetrachloride, hydrochloric acid or sulfuric acid at temperatures of from about 0 to 100 degrees Centigrade, preferably the catalyst employed being anhydrous aluminum chloride in the presence of hydrogen chloride gas employing benzene as a solvent. Particularly desirable reaction temperature is from about 40° to 80° C. and advantageously from 50° to 70° C. Dehydrogenation of compound (II) to compound (III) is readily accomplished with conventional dehydrogenation catalysts such as are employed in the preparation of styrene from ethyl benzene. Usually such catalysts are iron oxide (Fe$_2$O$_3$), potassium promoted generally in the form of the carbonate and chromium oxide stabilized. Catalysts suitable for the practice of the present invention are disclosed in the following U.S. Pat. Nos. 2,971,927; 3,084,125; 2,395,875; 2,395,876; 3,205,179; 3,360,579; 3,703,593; 4,143,083; 4,144,197; 4,149,996; 4,152,300.

In the preparation of the bis(1-phenylethyl)aromatic compounds by disproportionation in accordance with the present invention, mostly meta-bis(1-phenylethyl)benzene and para-bis(1-phenylethyl)benzene is produced. The meta isomer is most desirable for the preparation of lithium based polymerization initiating compounds, and therefore the para isomer may be recycled through the Friedel-Craft's disproportionation reaction to provide a more meta isomer. The meta and para isomers are readily separated by distillation. For compound (II) and n equal to 0, the meta isomer boils at about 178° to 180 ° C. under a pressure of 1.3 to 1.6 millimeters of mercury. The distilled meta isomer is readily purified by recrystallization from methyl alcohol.

The invention is further illustrated but not limited by the following example:

A 1-liter jacketed reaction flask was fitted with a magnetic stirrer and facilities to gas purge the vessel, also a jacketed addition funnel and a reflux condenser. Water having a temperature of 60° C. was circulated within the vessel and addition funnel jackets. The reaction vessel was charged with 351.5 grams of 1,1-diphenylethane and 190.5 grams of benzene. The magnetic stirrer was employed to agitate the reaction mixture. Vapor space above the liquid was purged with gaseous hydrogen chloride and 10.29 grams of anhydrous aluminum chloride were added. The aluminum chloride was weighed in a nitrogen atmosphere. During the reaction, several samples were withdrawn through a sampling septum and analyzed. The results are set forth in Table I.

TABLE I

| Reaction Time (min) | % 1,1DPE Conv. | meta/para[1] Ratio | Yield to meta & para | Yield to meta |
| --- | --- | --- | --- | --- |
| 17 | 37.5 | 47/54 | 60.6 | 28.5 |
| 30 | 49.2 | 55/45 | 49.5 | 27.2 |
| 42 | 53.3 | 56/44 | 46.1 | 25.8 |

[1]Meta = M—Bis(1-phenylethyl)benzene
Para = P—Bis(1-phenylethyl)benzene

Meta-Bis(1-phenylethyl)benzene was dehydrogenated employing a ¾-inch diameter 36-inch long reactor tube commercially available under the trade designation of Alley #446. The reactor contained 85 cubic centimeters, 134 grams, of 3/16 inch size iron oxide catalyst commercially available under the trade designation of S-330C-22.5. The meta-bis(1-phenylethyl)benzene was fed to the reactor at a rate of about 10 cubic centimeters per hour together with water at a rate of 135 centimeters per hour. Various temperatures were employed to determine the effect on conversion and yield. The results are set forth in Table II.

TABLE II

| Cut # | Reaction Temp. °C. | % 3-Ring Conv. | % Yield to Unsat-M—3-Ring[1] |
| --- | --- | --- | --- |
| 12 | 597 | 82.07 | 61.20 |
| 16 | 619 | 88.98 | 61.20 |
| 17 | 629 | 88.02 | 57.60 |

[1]Unsat-M—3 ring = M—Bis(1-phenylethenyl)benzene

The crude reaction mixture from the dehydrogenation weighed 317 grams and contained 43.2 weight percent meta-bis(1-phenylethenyl)benzene. The crude reaction mixture was charged to a 1-liter distillation flask together with 3 grams of a polymerization inhibitor believed to be 2,6-ditertiarybutyl-4-hydroxymethylphenol. The distillation column utilized had 20 plates, was equipped with reflux control, fraction cutter and a vacuum source. Distillation of the crude reaction mixture was carried out at pressures averaging from about 1.6 to about 1.3 millimeters of mercury as measured by a McLeod gauge. The reflux ratio during the distillation of the meta-bis(1-phenylethenyl)benzene was about 8:1. The meta-bis(1-phenyethenyl)benzene fraction was about 67.3 grams and was collected between 178° C. and 180° C. as measured at the top of the column. The crude product from the distillation was about 78.3 weight percent of the desired compound and crystallized at room temperature. A portion of the meta-bis(1-phenylethenyl)benzene was recrystallized by dissolving 10.3 grams in 49.2 grams of methyl alcohol. The mixture was heated to 55° C. to dissolve the substituted benzene and then cooled to 5° C. The resultant mixture was then poured into a Buchner funnel attached to a suction flask, the crystals collected and dried in a vacuum oven. 5.3 Grams of meta-bis(1-phenylethenyl)benzene of 99 weight percent purity as determined by gas chromatography were recovered. The melting point of the crystals was 44° to 45° C.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A method for the preparation of bis(1-phenylethenyl)aromatic compounds, the steps of the method comprising providing a 1,1-diphenylethane, disproportionating the 1,1-diphenylethane in the presence of a Friedel-Craft's catalyst to form a bis(1phenylethyl)aromatic compound and subsequently dehydrogenating the bis(1-phenylethyl)aromatic compound to a bis(1-phenylethenyl)aromatic compound.

2. The method of claim 1 wherein the disproportionation is carried out at a temperature of from about 0° to about 100° C.

3. The method of claim 2 wherein the disproportionation is carried out at a temperature of from about 40° to about 80° C.

4. The method of claim 3 wherein the disproportionation is carried out at a temperature of from about 50° to about 70° C.

5. The method of claim 1 wherein the Friedel-Craft's catalyst is aluminum chloride.

6. The method of claim 1 wherein each n is a zero.

7. The method of claim 1 wherein the dehydrogenation catalyst is primarily ferrate oxide.

8. The method of claim 1 including the step of recycling any para isomer the disproportionating step.

9. The method of claim 1 including the steps of serparating the desired bis(-phenylethenyl) compound of distillation.

* * * * *